(12) United States Patent
Yang et al.

(10) Patent No.: US 10,869,905 B2
(45) Date of Patent: Dec. 22, 2020

(54) COMPOSITION FOR TREATING CELLULITE, AND MICRONEEDLE INCLUDING SAME

(71) Applicant: PUSAN NATIONAL UNIVERSITY INDUSTRY-UNIVERSITY COOPERRATION FOUNDATION, Busan (KR)

(72) Inventors: Seung Yun Yang, Daegu (KR); Beum Soo An, Busan (KR); Keum Yong Seong, Busan (KR); Sung Min An, Yeongcheon (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 16/329,553

(22) PCT Filed: Aug. 29, 2017

(86) PCT No.: PCT/KR2017/009401
§ 371 (c)(1),
(2) Date: Feb. 28, 2019

(87) PCT Pub. No.: WO2018/044022
PCT Pub. Date: Mar. 8, 2018

(65) Prior Publication Data
US 2019/0192611 A1    Jun. 27, 2019

(30) Foreign Application Priority Data

Aug. 31, 2016 (KR) .................. 10-2016-0111708
Aug. 25, 2017 (KR) .................. 10-2017-0107732

(51) Int. Cl.
*A61K 38/01* (2006.01)
*A61P 3/04* (2006.01)
*A61K 9/00* (2006.01)
*A61M 37/00* (2006.01)

(52) U.S. Cl.
CPC .......... *A61K 38/014* (2013.01); *A61K 9/0021* (2013.01); *A61P 3/04* (2018.01); *A61M 37/0015* (2013.01); *A61M 2037/0023* (2013.01)

(58) Field of Classification Search
CPC .. A61K 9/0014; A61K 38/014; A61K 9/0021; A61P 3/04
See application file for complete search history.

(56) References Cited

U.S. PATENT DOCUMENTS 7,282,220 B1    10/2007   Sung et al.
2002/0025340 A1 *  2/2002  Dyer .................... A61K 9/0019
                                                            424/486

FOREIGN PATENT DOCUMENTS

| EP | 0028374 | 5/1981 |
| JP | 2007/254440 | 10/2007 |
| JP | 2009/102233 | 5/2009 |
| WO | WO 2015/186940 | 12/2015 |

OTHER PUBLICATIONS

Duke University Libraries, What's gelatin made of?, Mar. 12, 2007, available online at: https://blogs.library.duke.edu/answerperson/2007/03/12/gelatin. (Year: 2007).*
Ratnayake et al. "Influence of Dietary Protein and Fat on Serum Lipids and Metabolism of Essential Fatty Acids in Rats" *British Journal of Nutrition*, 1997; 78, 459,467.
International Search Report and Written Opinion issued in Application No. PCT/KR2017/009401, dated Nov. 29, 2017 (English translation of Search Report Provided).
Gabr et al., "Effect of gelatin infusions on blood serum lipid pattern." *Arzneimittelforschung*. 1990, 40(7): 761-762.

* cited by examiner

*Primary Examiner* — James H Alstrum-Acevedo
*Assistant Examiner* — Kaipeen E Yang
(74) *Attorney, Agent, or Firm* — Norton Rose Fulbright US LLP

(57) ABSTRACT

In a composition and a microneedle for a localized obesity treatment containing the same in accordance with the present disclosure, the composition in accordance with the present disclosure contains a gelatin, decomposes a fat in a body, and inhibits lipogenesis and fat deposition in the body.

12 Claims, 8 Drawing Sheets

COMPOSITION FOR TREATING CELLULITE, AND MICRONEEDLE INCLUDING SAME

This application is a national phase application under 35 U.S.C. § 371 of International Application No. PCT/KR2017/009401, filed Aug. 29, 2017, which claims priority to Korean. Provisional Application Number 10-2016-0111708 filed Aug. 31, 2016, and Korean. Provisional Application Number 10-2017-0107732 filed Aug. 25, 2017. The contents of the referenced applications are incorporated into the present application by reference.

FIELD OF THE INVENTION

The present disclosure relates to a composition for treatment of an obesity, and more particularly, to a composition for treatment of a localized obesity and a microneedle for a localized obesity treatment containing the same.

BACKGROUND

A localized obesity refers to an obesity that occurs mainly in local regions such as arms, sides, thighs, and the like. A cellulite may be an example of the localized obesity. An interest in methods for treating the localized obesity of modern women who are interested in beauty is increasing. Major localized obesity treatment methods currently being executed includes an injection method for injecting a drug that directly decompose a fat in a selected region and a drug that smooths a blood circulation, a surgical method, such as a liposuction for directly extracting a fat in the body, and a method using various special treatment equipment such as a high frequency treatment. However, these treatment methods may be costly, and cause side effects such as a pain, a scar, and the like. Further, only temporary effects may be exhibited.

In order to solve the problems of the conventional localized obesity treatment methods, a method for defining a small hole in a skin with a microneedle and applying a drug therein is used. However, an absorption rate of the drug is so low that the method does not show an effective lipolysis. Therefore, there is a need for a further study on the microneedle for the obesity treatment which may solve this problem and has an excellent obesity treatment effect.

SUMMARY OF THE INVENTION

A purpose of the present disclosure is to provide a composition that may be injected into a body to treat an obesity.

Another purpose of the present disclosure is to provide a microneedle for a localized obesity treatment containing the composition.

In one aspect, there is provided a composition containing a gelatin, wherein the composition decomposes a fat in a body, and inhibits lipogenesis and fat-deposition in the body.

In one embodiment, the composition may be intended for a hypodermic injection or may be contained in a microneedle.

In another aspect, there is provided a microneedle for treatment of a localized obesity containing any of the above compositions, wherein the microneedle inhibits lipogenesis and fat-deposition in the body.

In one embodiment, when the microneedle is applied onto a skin, a tip portion of the microneedle may be located below the skin stratum corneum, wherein the tip portion may contain the composition containing the gelatin and may be decomposed at a position below the skin stratum corneum such that the gelatin may locally decompose a fat and inhibit lipogenesis and fat-deposition around a region where the microneedle is located.

In one embodiment, the gelatin may be cross-linked. In this connection, the gelatin may be cross-linked using genipin.

In one embodiment, the microneedle may release the composition containing the gelatin in a sustained manner. In this connection, the sustained release may last for at least three days.

In one embodiment, the gelatin may include an animal-derived gelatin.

In this connection, the animal-derived gelatin may include a swine-derived gelatin.

In a composition and a microneedle for a localized obesity treatment containing the same in accordance with the present disclosure, the composition in accordance with the present disclosure contains a gelatin, thereby decomposing a fat in a body, and inhibiting a lipogenesis and a fat deposition in the body. Further, when the microneedle containing the composition in accordance with the present disclosure is applied to the skin, the microneedle may release the composition into the body by absorbing body fluid. Thus, a fat around a region where the microneedle in accordance with the present disclosure is injected may be decomposed with an excellent efficiency, and the lipogenesis and the fat deposition may be inhibited. Therefore, the obesity may be treated locally. The composition and the microneedle in accordance with the present disclosure may use the gelatin, which is cheap and easily available, such that the obesity may be treated easily and economically.

BRIEF DESCRIPTION OF THE DRAWINGS

FIG. 5 is a diagram for illustrating an inhibition of an animal panniculus adiposus deposition of a microneedle in accordance with the present disclosure.

DETAILED DESCRIPTION OF THE INVENTION

Hereinafter, embodiments of the present disclosure will be described in detail with reference to the accompanying drawings. The present disclosure may be changed in various ways, and may be implemented in various forms. Examples of various embodiments are illustrated and described further below. It will be understood that the description herein is not intended to limit the present disclosure to the specific embodiments described. On the contrary, it is intended to cover alternatives, modifications, and equivalents as may be included within the spirit and scope of the present disclosure. Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Hereinafter, the terminology used in the present application is for the purpose of describing particular embodiments only and is not intended to be limiting the present disclosure. As used herein, the singular forms "a," "an," and "the" are intended to include the plural forms as well, unless the context clearly indicates otherwise. It will be further understood that the terms "comprises," "comprising," "includes," and "including," when used in the present application, specify the presence of the stated features, steps, operations, elements, components, and/or combinations thereof, but do not preclude the presence or addition of one or more other features, steps, operations, elements, components, and/or combinations thereof.

Unless otherwise defined, all terms including technical and scientific terms used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A composition for a localized obesity treatment in accordance with the present disclosure contains a gelatin, decomposes a fat in a body when injected into the body, and inhibits a lipogenesis and a fat deposition in the body.

A gelatin is a kind of a derived protein obtained by treating a collagen, which is a natural protein constituting animal skin, tendon, cartilage, and the like, with hot water. The gelatin in accordance with the present disclosure may be a gelatin obtained from an animal such as a cow, a swine, and the like, or a gelatin obtained from a squid or a fish. In one example, the gelatin may be a swine-derived gelatin obtained from the swine.

In this connection, the gelatin may be a cross-linked gelatin. The gelatin may be cross-linked via a cross-linked bond between amine groups that the gelatin contains. The gelatin may be cross-linked in a variety of ways. In one example, the cross-link of the gelatin may be a cross-link due to a cross-linking agent. In one example, the cross-linking agent may be a genipin. The cross-linked gelatin may be decomposed more sustainedly than the gelatin in the body, and a release speed of the gelatin in the body may be adjusted by adjusting a cross-link degree of the gelatin. In addition, a speed of the lipolysis may be adjusted based on the release speed of the gelatin.

A composition containing the gelatin in accordance with the present disclosure may include a composition for a hypodermic injection for a direct in vivo injection or a composition for producing a microneedle for an in vivo injection. That is, the gelatin-containing composition may be injected directly into the living body or may be produced as the microneedle such that the gelatin may be injected into the living body by a decomposition of the microneedle. Therefore, a fat present in a periphery of an injected region of the composition may be decomposed, and the lipogenesis and the fat deposition may be suppressed.

In this connection, the composition may include components such that physical properties and concentrations of the gelatin in the composition suitable for the gelatin injection into the living body or for the microneedle production may be achieved. The components may include any component that does not limit the lipolysis, lipogenesis and fat deposition inhibitory effects, and is suit for a human body. In one example, the components may include a polymer, a cross-linking agent, a plasticizer, or a solvent.

The microneedle in accordance with the present disclosure contains the composition containing the gelatin in accordance with the present disclosure.

The microneedle refers to a needle of a fine size. The microneedle may include a microneedle structure alone, or alternatively may further include a patch layer that has a flat face on which the microneedle structure is disposed. The patch layer may not be inserted into a skin, but is in contact with and adhered to a skin surface when the microneedle is applied onto the skin. The patch layer may exhibit elasticity and flexibility, and thus may be deformed to conform to a curved skin surface. The microneedle may be disposed on the patch layer independently, or may be a plurality of microneedles may be disposed thereon.

A length of the microneedle may be equal to or greater than a thickness of a skin stratum corneum in order to be located below the skin stratum corneum when applied to the skin. The stratum corneum of the skin is an outermost layer of an epidermis that constitutes the skin. The stratum corneum protects the skin from an external environment, and prevents an evaporation of water in the body to maintain a homeostasis of the human body. The skin epidermis in which the stratum corneum is located varies in thickness from the thinnest eyelid (average 0.04 mm) to the thickest hand or sole (average 1.6 mm), and usually has a thickness of 0.05 to 0.1 mm, of which the stratum corneum has an average thickness of 0.01 mm to 0.03 mm (10 µm to 30 µm). Thus, a length of the microneedle in accordance with the present disclosure may be equal to or greater than 10 µm, which is a length equal to or greater than a general minimum thickness of the stratum corneum. In one example, a length of the microneedle may be in a range of 10 µm to 300 µm, which is a range equal to or greater than a thickness of the stratum corneum, and may reach a dermis below the epidermis. Alternatively, a length of the microneedle in accordance with the present disclosure may be a few millimeters (mm) to a few centimeters (cm) in length, which is a length that may pass through the dermis to reach the panniculus adiposus. That is, a length of the microneedle in accordance with the present disclosure may range in length from a few micrometers (µm) to a few millimeters (mm), or to a few centimeters (cm). The microneedle in accordance with the present disclosure has a length equal to or greater than a thickness of the skin stratum corneum. Therefore, when the microneedle is applied to the skin, a tip portion of the microneedle is located at a skin tissue below the skin stratum corneum. Then, in the skin tissue, the microneedle may be degraded (biodegraded) by an internal component such as a moisture or an enzyme to transfer the composition containing the gelatin in accordance with the present disclosure contained in the microneedle to the skin tissue. Therefore, the fat around the regions where the microneedle in accordance with the present disclosure is applied may be locally decomposed, and the lipogenesis and the fat deposition may be suppressed. More specific localized obesity treatment by the application of the microneedle in accordance with the present disclosure will be described with reference to FIG. 2.

Figure 1:
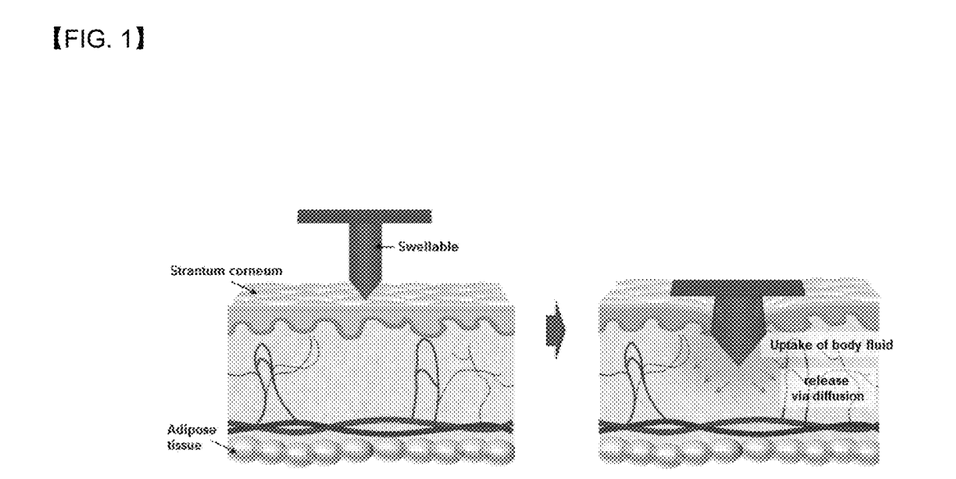
FIG. 1 illustrates a microneedle in accordance with the present disclosure.

FIG. 1 illustrates a microneedle in accordance with the present disclosure.

In a detailed description of the gelatin release of the microneedle in accordance with the present disclosure with reference to FIG. 1, when the microneedle penetrates into the skin, a sharp tip of the microneedle, that is, the tip portion is positioned below the skin stratum corneum. In this connection, the tip portion of the microneedle contains the composition containing the gelatin, and is swollen and decomposed by body fluids. Thus, the composition containing the gelatin may be released to a skin tissue below the skin stratum corneum. Therefore, around the region where the microneedle is located in the body, the fat may be decomposed or the lipogenesis and the fat deposition may be repressed by the gelatin released resulting from the degradation of the microneedle. That is, the microneedle in accordance with the present disclosure may decompose the fat around the region where the microneedle is applied, and may repress the lipogenesis and the fat deposition. Thus, the microneedle in accordance with the present disclosure may be applied to the skin to treat the localized obesity of the skin to which the microneedle is applied.

In this connection, the microneedle may release the gelatin-containing composition for three days or more. In one example, when the gelatin is the cross-linked gelatin, it may be released for a long time compared to a non-cross-linked gelatin.

Hereinafter, an anti-obesity effect of the composition and the microneedle in accordance with the present disclosure will be described in detail with specific embodiments.

First, in order to confirm the localized obesity treatment effect of the composition in accordance with the present disclosure, the gelatin-containing composition was produced, and an anti-obesity activity thereof was evaluated. An artificially differentiated adipocytes were extracted from an adipose tissue of a 6-week-old Sprague-Dawley male rat of a weight of about 170 g. Then, the differentiated adipocytes were treated with the gelatin-containing composition in accordance with the present disclosure (hereinafter, a gelatin composition). Then, mRNA and protein expression levels of lipogenesis and adipocyte production-related genes in the differentiated adipocytes were examined to determine the anti-obesity activity. In this connection, results of a gelatin concentration of 0.1 mg/ml (Gelatin 0.1×) in the gelatin composition are shown in FIG. 2.

Figure 2:
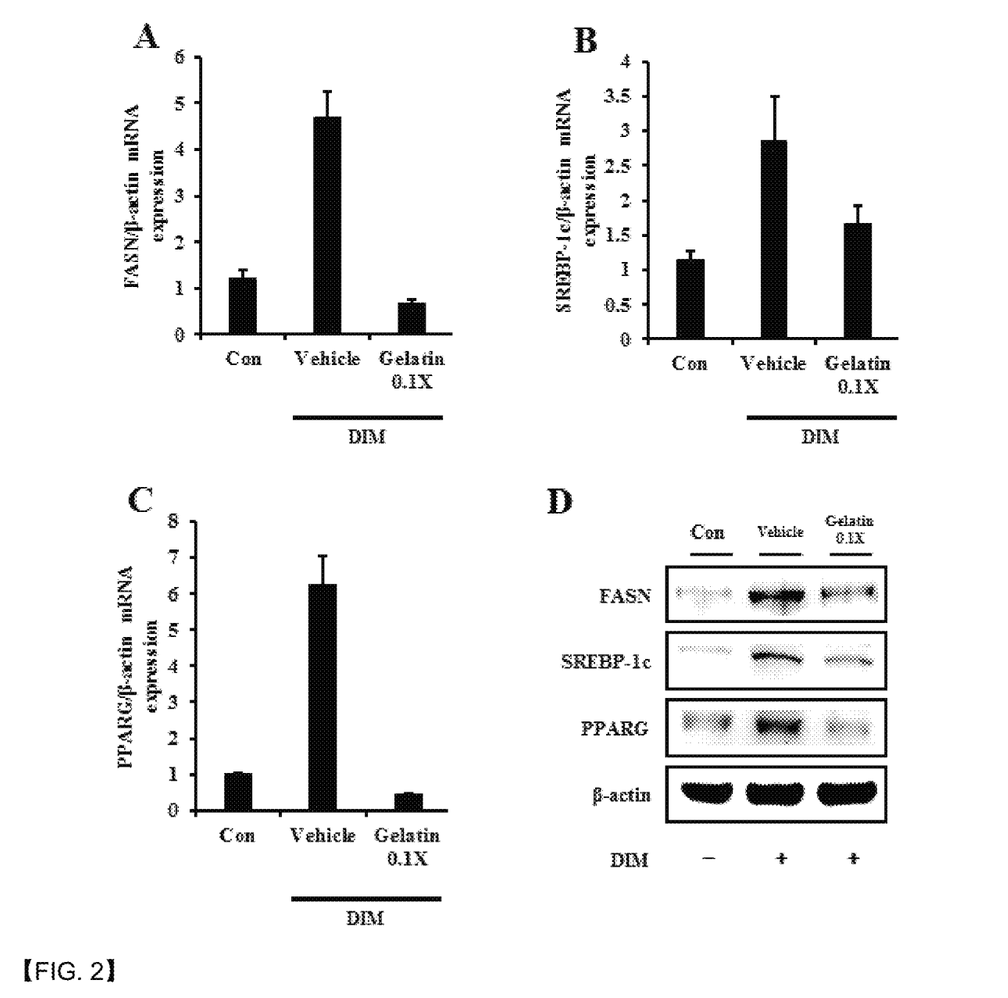
FIG. 2 is a diagram for illustrating an effect of inhibiting a lipogenesis of a composition in accordance with the present disclosure.

FIG. 2 is a diagram for illustrating an effect of inhibiting a lipogenesis of a composition in accordance with the present disclosure, and is a diagram for illustrating the anti-obesity activity of the composition in accordance with the present disclosure at in vitro level.

A in FIG. 2 is a diagram for illustrating mRNA expression levels of FASN, which is a fat synthetase. Further, B and C in FIG. 2 are diagrams for respectively illustrating mRNA expression levels of SREBP-1c, and PPARG, which are proadipogenic transcription factors. Further, D in FIG. 2 is a diagram for illustrating protein expression levels of the FASN, the SREBP-1c, and the PPARG.

In FIG. 2, "Con" represents a normal preadipocyte cell as a control group, "DIM" represents 10 µM dexamethasone, 5 µg/ml insulin, and 0.5 mM iso-butyl-methyl-xanthine (IBMX) as substances added to differentiate the preadipocyte cell into the adipocyte, "Vehicle" represents a normal, differentiated adipocyte as a control group, and "Gelatin" represents the gelatin.

With reference to A in FIG. 2, it may be confirmed that, after treating with the gelatin composition, the mRNA expression level of the FASN, which is the fat synthetase, is reduced. In particular, it may be confirmed that the expression level is lower than that of the normal preadipocyte cell. This means that the gelatin may reduce the expression of the fat synthase at a transcriptional level and thus exhibit the effective anti-obesity activity.

With reference to B in FIG. 2, it may be confirmed that the mRNA expression level of the SREBP-1c, the proadipogenic transcription factor involved in a regulation of the adipocyte differentiation, is reduced when treated with the gelatin composition. In addition, it may be confirmed that the mRNA expression is significantly reduced compared to the Vehicle, and is reduced to a value similar to that of an undifferentiated preadipocyte cell.

With reference to C in FIG. 2, it may be confirmed that, when the PPARG, the proadipogenic transcription factor involved in a regulation of a different adipocyte differentiation and a specific marker of the adipocyte differentiation, is treated with the gelatin composition, the mRNA expression level of the PPARG is significantly reduced, and is lower than the expression level of the undifferentiated preadipocyte cell.

Further, with reference to D in FIG. 2, in order to confirm a regulation of these genes in terms of a translation level, a western blot analysis is executed on protein expression levels of the FASN, the SREBP-1c, and the PPARG under presence and absence (Vehicle) of the gelatin composition. It may be confirmed from the western blot analysis that, as shown in A to C in FIG. 2, the analysis result is consistent with the decrease in the mRNA expression level after the treatment with the gelatin composition.

Collectively, as described above, it may be confirmed that the FASN, which is the fat synthetase, and the SREBP-1c, and the PPARG, which are the proadipogenic transcription factor were regulated at transcription and translation levels by the gelatin-containing composition in accordance with the present disclosure, thereby reducing the protein expression. This means that the gelatin-containing composition in accordance with the present disclosure effectively exhibits the anti-obesity activity.

In addition, in order to further confirm the lipolytic effect of the gelatin composition, mature adipocytes were separated from the adipose tissue of the Sprague-Dawley male rat of a weight of about 170 g. Then, 0.1 mg/ml (0.1×), 1 mg/ml (1×), and 2 mg/ml (2×) of gelatin compositions were added to the separated adipocytes. Thereafter, the gelatin composition added adipocytes were incubated for 24 hours. The results are shown in FIG. 3.

Figure 3:
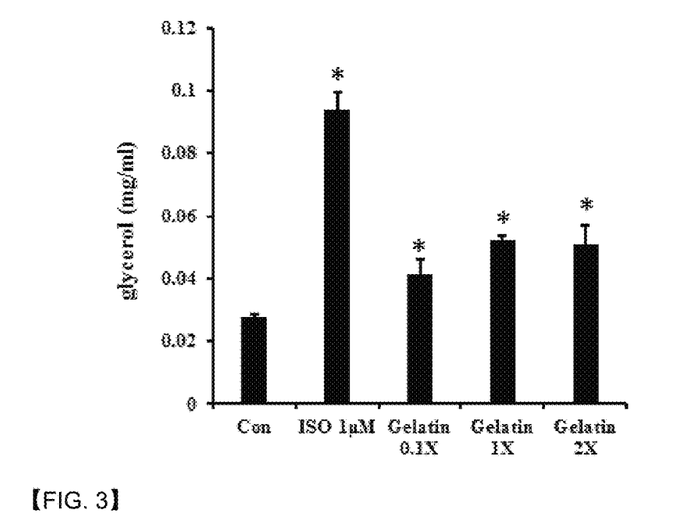
FIG. 3 is a diagram for illustrating a lipolytic effect of a composition in accordance with the present disclosure.

FIG. 3 is a diagram for illustrating a lipolytic effect of a composition in accordance with the present disclosure.

FIG. 3 illustrates glycerol concentrations after treating with various concentrations of the gelatin composition. In FIG. 3, "Con" represents a normal adipocyte as a control group, "ISO 1 µM" represents an injection of 1 µM isoproterenol, a drug specifically acting on β-receptors that promote the lipolysis, and "Gelatin" represents the gelatin.

With reference to FIG. 3, at concentrations of 0.1×, 1×, and 2× of the gelatin composition, glycerol concentrations were respectively 1.51 times, 1.9 times, and 1.84 times higher than that of control group cells. This means that the gelatin stimulated the lipolysis, and consequently the concentration of the glycerol increased.

Thus, it may be confirmed that the gelatin composition in accordance with the present disclosure plays an important role in stimulating the lipolysis in the adipose tissue.

Next, in order to confirm the anti-obesity activity of the microneedle in accordance with the present disclosure, microneedles respectively containing compositions in accordance with the present disclosure containing a non-cross-linked gelatin and a gelatin cross-linked using genipin were produced. Then the panniculus adiposus deposition inhibitory effect was confirmed using the microneedle. Microneedles produced with compositions respectively containing the non-cross-linked gelatin and 0.25% and 1.0% (percentage of the cress-linking agent (genipin) relative to the gelatin) gelatin (gelpin) as cross-linked using the genipin were attached to a skin of the rats for 2 days. Two days after the attachment of each microneedle, body weight changes of the rats and weight changes of the adipose tissues were observed. The results are shown in FIG. 4.

Figure 4:
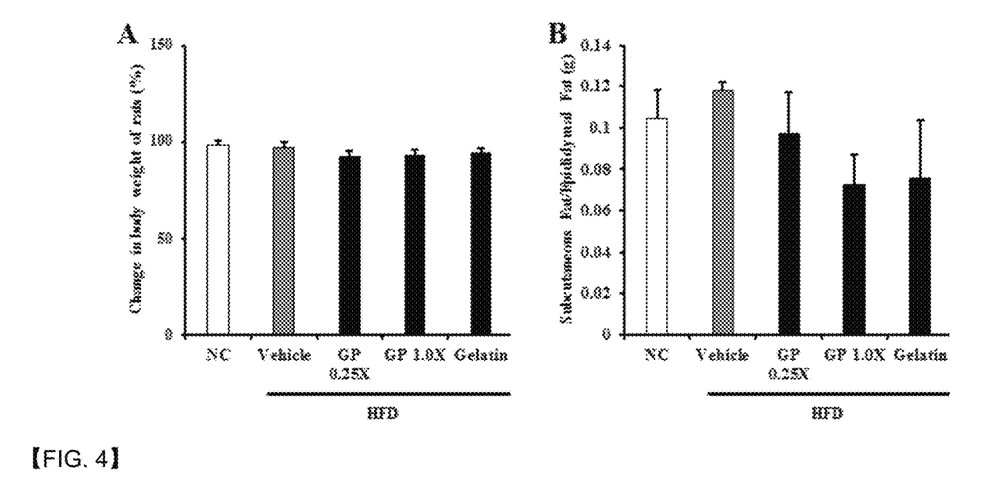
FIG. 4 is a diagram for illustrating an inhibition of an animal panniculus adiposus deposition of a microneedle in accordance with the present disclosure.

FIG. 4 is a diagram for illustrating an inhibition of an animal panniculus adiposus deposition of a microneedle in accordance with the present disclosure.

A in FIG. 4 illustrates body weight changes of the rats having the microneedles attached thereto, and B in FIG. 4 illustrates weight changes of the panniculus adipose tissue of the rats having the microneedles attached thereto.

In FIG. 4, "NC" represents a normal feed-fed rat, and "HFD" represents high-fat feed-fed rats. "Vehicle" represents a high-fat feed-fed rat as a control group, "GP" represents the gelpin that refers to cross-linked gelatin, and "Gelatin" represents the gelatin.

With reference to A in FIG. 4, it may be confirmed that the body weights of the rats did not change significantly in all of the microneedles.

With reference to B in FIG. 4, it may be seen that weight losses of the panniculus adipose tissue appear in the microneedles in accordance with the present disclosure. It may be further confirmed that all of the microneedles respectively containing the gelatin, 0.25% gelpin, and 1% gelpin in accordance with embodiments of the present disclosure were able to reduce the weight levels of the panniculus adipose tissue of the high-fat feed-fed rats to or below a weight level of the panniculus adipose tissue of the normal rat.

In order to confirm a sustained effect of the microneedle in accordance with the present disclosure, the gelpin-containing microneedles were attached to the rats for 3 days. The results are shown in FIG. 5.

FIG. 5 is a diagram for illustrating an inhibition of an animal panniculus adiposus deposition of a microneedle in accordance with the present disclosure.

A in FIG. 5 illustrates body weight changes of the rats attached with the microneedles, and B in FIG. 5 illustrates weight changes of the panniculus adipose tissues of the rats attached with the microneedles.

In FIG. 5, "NC" represents the normal feed-fed rat, and "HFD" represents the high-fat feed-fed rats. "Vehicle" represents the high-fat feed-fed rat as a control group, and "GP" represents the gelpin that refers to the cross-linked gelatin.

With reference to FIG. 5, it may be confirmed that, when the microneedles were attached for 3 days, there was no significant change in the overall body weight, as with the second day, but the weight of the panniculus adipose tissue at a region where the microneedle was applied was reduced more than that the second day. This means that the microneedle may continuously exhibit a long-term lipolytic effect.

That is, with reference to FIG. 4 again together with FIG. 5, it may be confirmed that the microneedle in accordance with the present disclosure may, regardless of the overall body weight change of the rat, partially reduce the weight of the panniculus adipose around the microneedle, which may last for a long time.

Further, in order to confirm an adipocyte size reducing effect of the microneedle, histological changes in the adipose tissues were observed. The adipose tissues were fixed with paraffin, and stained with H&E. Next, images of the stained adipocytes were captured with an optical microscope, and the numbers of cells were measured in diagrams. Fat deposition rates were calculated based on the numbers of the adipocytes in a restricted region. The results are shown in FIG. 6.

Figure 6:
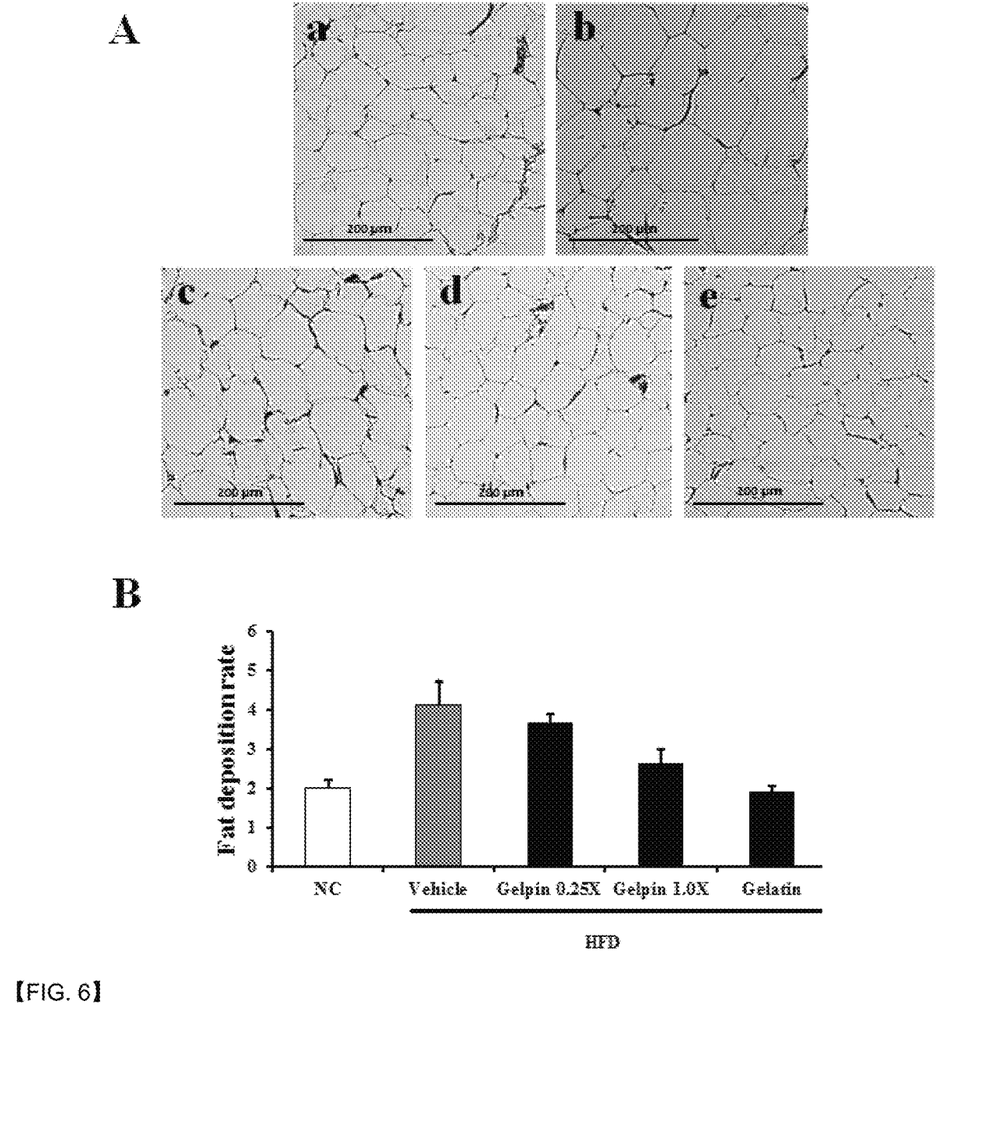
FIG. 6 is a diagram illustrating a reduction of a fat deposition rate in an adipose tissue by a microneedle in accordance with the present disclosure.

FIG. 6 is a diagram illustrating a reduction of a fat deposition rate in an adipose tissue by a microneedle in accordance with the present disclosure.

A in FIG. 6 shows photographs of the adipocytes captured by a microscope. In A in FIG. 6, a represents an adipocyte of a normal feed-fed rat, b represents an adipocyte of a high-fat feed-fed rat, and c represents an adipocyte of a high-fat feed-fed rat when the 0.25% gelpin-containing microneedle was applied. d represents an adipocyte of a high-fat feed-fed rat when the 1.0% gelpin-containing microneedle was applied, and e represents an adipocyte of a high-fat feed-fed rat when the gelatin-containing microneedle is applied.

B in FIG. 6 is a diagram illustrating calculated fat deposition rates. In B in FIG. 6, "NC" represents the normal feed-fed rat, and "HFD" represents the high-fat feed-fed rats. "Vehicle" represents the high-fat feed-fed rat as a control group, "GP" represents the gelpin that refers to the cross-linked gelatin, and "Gelatin" represents the non-cross-linked gelatin.

With reference to A in FIG. 6, it may confirmed that the Vehicle, the adipocyte of the high-fat feed-fed rat, has a size larger than that of the normal rat adipocyte, and the microneedle in accordance with the present disclosure reduces a size of the adipocyte in the high-fat feed-fed rat in comparison to the Vehicle. In particular, it may be confirmed that the gelatin microneedle may reduce the size of the adipocyte in the high-fat feed-fed rat to a normal rat level. This is because, in comparison with the gelatin, the gelpin-containing microneedle was cross-linked such that the gelatin was released in a sustained manner, thus relatively small amount thereof was released in the same amount of time. It may be expected that, when the gelpin-containing microneedle is attached for a long time, an excellent adipocyte size reduction effect may occur.

With reference to B in FIG. 6, it may be confirmed that the fat deposition rates are also exhibit results consistent with the histological analysis that compares adipocyte sizes.

Thus, it may be confirmed that the microneedle according to the present disclosure may effectively reduce the size of the adipocyte, and also reduce the fat deposition rate. That is, it may be confirmed that the microneedle according to the present disclosure may exhibit the anti-obesity characteristics.

Subsequently, an influence of the microneedle on an expression of a transcriptional regulator of the adipose tissue was observed. The results are shown in FIG. 7.

Figure 7:
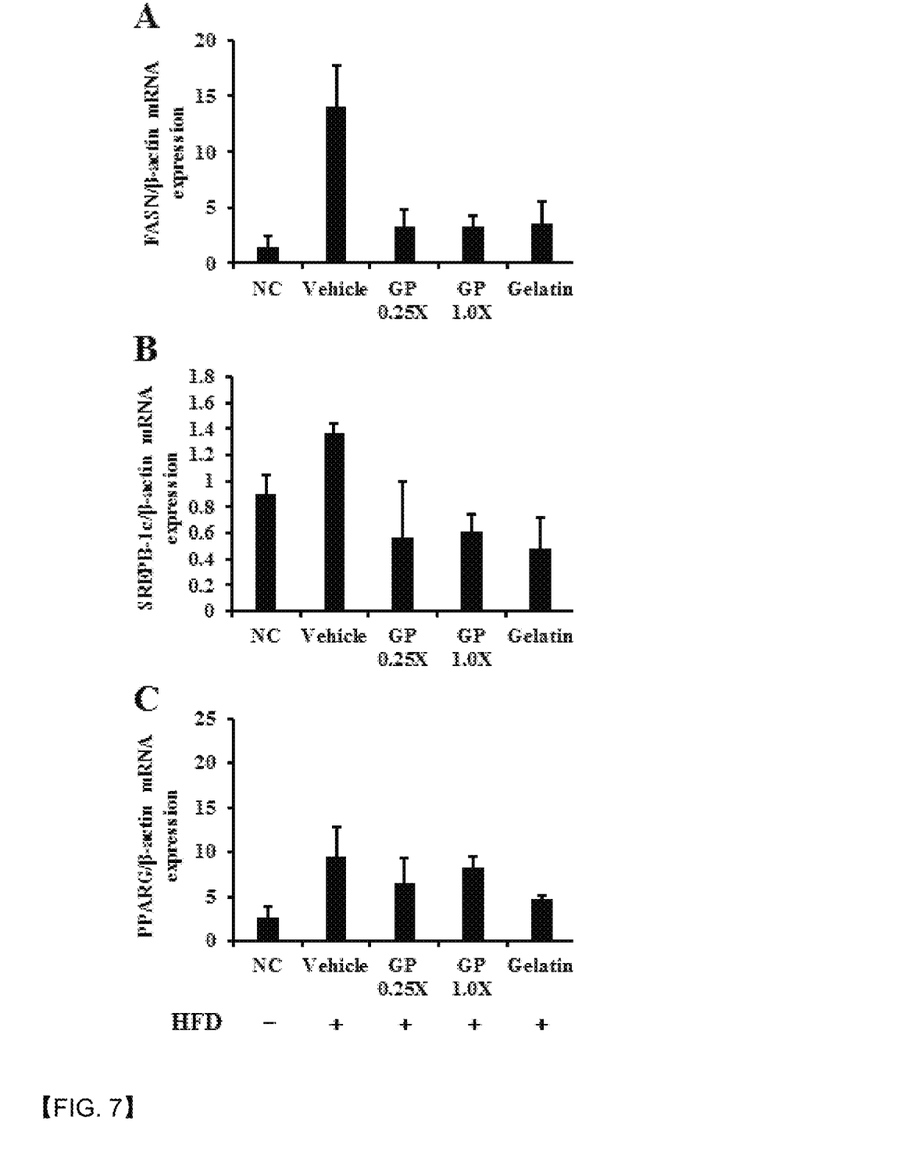
FIG. 7 is a diagram illustrating an anti-obesity effect of a microneedle in accordance with the present disclosure on a lipometabolism-related gene in an adipose tissue.

FIG. 7 is a diagram illustrating an anti-obesity effect of a microneedle in accordance with the present disclosure on a lipometabolism-related gene in an adipose tissue.

A in FIG. 7 is a diagram for illustrating FASN expressions based on the microneedles, B in FIG. 7 is a diagram for illustrating SREPB-1c expressions based on the microneedles, and C in FIG. 7 is a diagram for illustrating PPARG expressions based on the microneedles.

In FIG. 7, "NC" represents the normal feed-fed rat, "HFD" represents the high-fat feed-fed rats, and "Vehicle" represents the high-fat feed-fed rat as a control group. "GP" represents the gelpin that refers to cross-linked gelatin, and "Gelatin" represents the gelatin.

With reference to A in FIG. 7, it may be confirmed that the microneedles in accordance with the present disclosure reduced the expressions of the FASN, which is the fat enzyme, in the panniculus adipose tissue.

With reference to B in FIG. 7, it may be confirmed that the expressions of the SREBP-1c in the panniculus adipose tissue were significantly reduced after the treatment with the microneedle, thereby showing values lower than an expression level of the normal rat.

With reference to C in FIG. 7 it may be confirmed that, in the case of the PPARG, all of the microneedle in accordance with the present disclosure reduced the expressions of PPARG.

Thus, it may be confirmed that the microneedle according to the present disclosure may control the expressions of the adipose tissue transcription factors at the transcription level. That is, it may be confirmed, by reducing the expression of the adipose tissue transcription factor of the obese rat, that the expression of the adipose tissue transcription factor may be controlled to be a level similar to that of the normal rat. This means that the microneedle in accordance with the present disclosure may treat the obesity.

In order to confirm a more direct effect of the microneedle in accordance with the present disclosure, distributions and volumes of the panniculus adipose tissues were observed using a micro-CT. The results are shown in FIG. 8.

Figure 8:
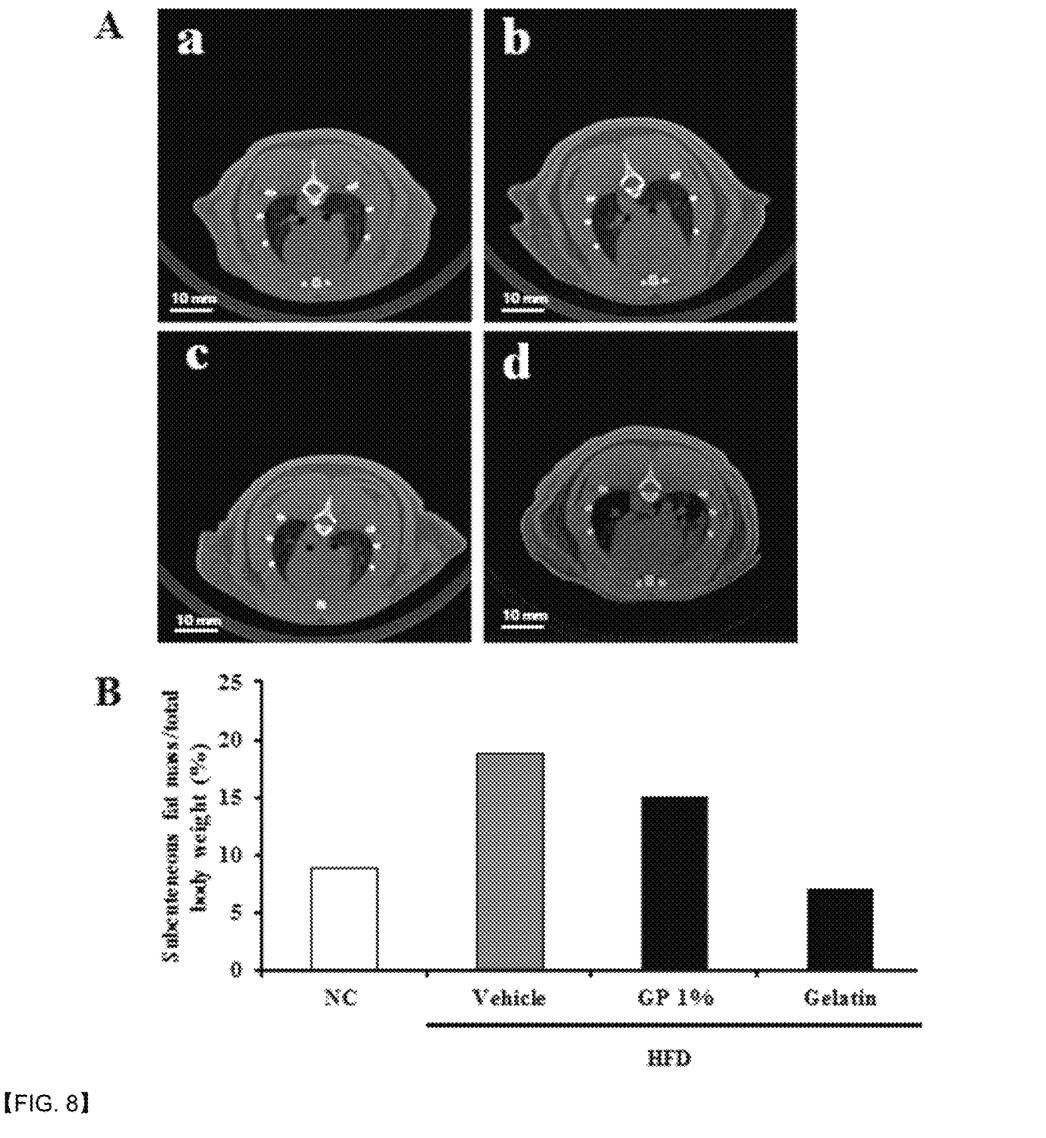
FIG. 8 is a diagram illustrating a distribution and a volume change of a panniculus adipose tissue by a microneedle in accordance with the present disclosure.

FIG. 8 is a diagram illustrating a distribution and a volume change of a panniculus adipose tissue by a microneedle in accordance with the present disclosure.

A in FIG. 8 shows photographs of the adipose tissues captured with the micro-CT. In A in FIG. 8, a represents the normal feed-fed rat, b represents the high-fat feed-fed rat, c represents a case where the 1.0% gelpin-containing microneedle was applied to the high-fat feed-fed rat, and d represents a case where the gelatin microneedle was applied to the high-fat feed-fed rat.

B in FIG. 8 is a diagram for quantifying regions of the panniculus adipose tissues. In B in FIG. 8, "NC" represents the normal feed-fed rat, "HFD" represents the high-fat feed-fed rats, and "Vehicle" represents the high-fat feed-fed rat as a control group. "GP" represents the gelpin that refers to the cross-linked gelatin, and "Gelatin" represents the gelatin.

With reference to FIG. 8, it may be confirmed that the areas of the panniculus adipose tissues were more reduced using the gelatin and 1.0% gelpin-containing microneedles than using other microneedles. An extent at which the area decreases using the gelpin-containing microneedle was lower compared to that using the gelatin-containing microneedle. However, this is due to a slow release in the body of the gelpin as the cross-linked gelatin. Therefore, it may be expected that when a sufficient time lapses, an extent at which the panniculus adipose tissue area deceases using the gelpin-containing microneedle increases.

That is, it may be confirmed that the microneedle in accordance with the present disclosure may reduce the panniculus adipose tissue at the region where the microneedle is applied, and the gelpin may be released in a sustained manner in the body based on a degree of the cross-link, thereby showing a long-term effect.

In addition, an anti-obesity activity of the gelatin composition in accordance with the present disclosure, as an injectable composition. Six-week old Sprague-Dawley male rats weighing about 170 g were fed the normal and high-fat feeds for six weeks, respectively. Thereafter, in order to determine abdominal fat deposition inhibition and decomposition effects, gelatin compositions respectively containing gelatins having concentrations of 10 mg/kg, 100 mg/kg, and 150 mg/kg were respectively injected to peritoneal cavities of the rats via an intraperitoneal injection for 5 weeks. Thereafter, body weight changes of the rats and weight changes of the abdominal adipose tissue were observed. The results are shown in FIG. 9.

Figure 9:
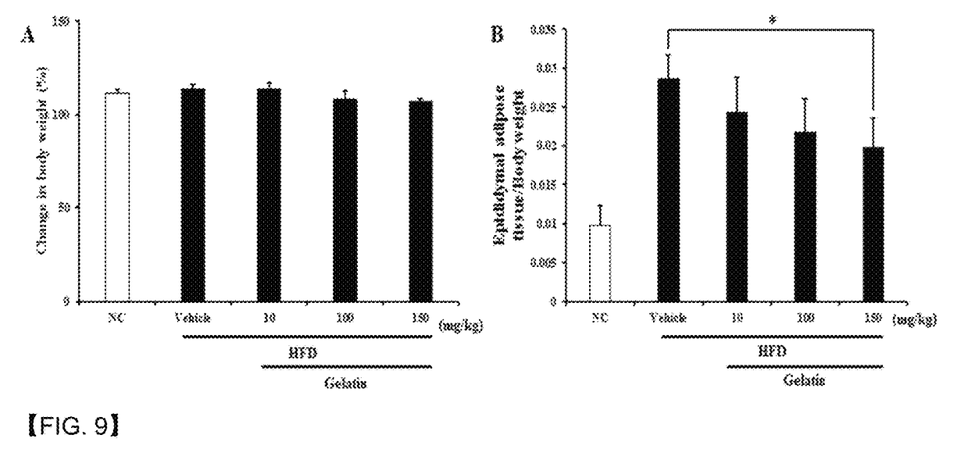
FIG. 9 is a diagram illustrating an inhibition of an abdominal fat deposition of a gelatin composition in accordance with the present disclosure.

FIG. 9 is a diagram illustrating an inhibition of an abdominal fat deposition of a gelatin composition in accordance with the present disclosure.

A in FIG. 9 illustrates the changes in body weight of the rats, and B in FIG. 9 illustrates the changes in weight of the adipose tissues of the abdominal parts of the rats.

In FIG. 9, "NC" represents the normal feed-fed rat, "HFD" represents the high-fat feed-fed rats. "Vehicle" represents the high-fat feed-fed rat as a control group, and "Gelatin" represents the gelatin.

With reference to A in FIG. 9, it may be confirmed that, comparing with the Vehicle showing a body weight change of the high-fat feed-fed rat, the body weights of the rats were slightly decreased based on a concentration of the gelatin when the gelatin composition in accordance with the present disclosure was injected. However, there was no statistical significance.

Further, with reference to B in FIG. 9, it may be confirmed that, comparing with the weight of the abdominal adipose tissue of the high-fat feed-fed rat, as the gelatin compositions in accordance with the present disclosure were injected via the intraperitoneal injection, the weights of the abdominal adipose tissues decreased. Further, in particular, it may be confirmed that the weights of the abdominal adipose tissues of the high-fat feed-fed rats respectively injected with the 10, 100, and 150 mg/kg concentrations of the gelatin decreased concentration-dependently.

This means, when the gelatin composition according to the present disclosure is injected as an injectable composition, that the fat is partially decomposed in the region where the gelatin composition in accordance with the present disclosure is injected while the overall body weight does not change much. Through this, it may be confirmed that the gelatin composition according to the present disclosure may be used as the injectable composition capable of exhibiting the anti-obesity activity locally.

Therefore, as described above with reference to FIG. 2 to FIG. 9, it may be confirmed that the gelatin-containing composition according to the present disclosure may exhibit the anti-obesity activity at the transcription and translation levels of the adipocyte and the adipose tissue, and may treat the obesity through the lipolysis and the fat deposition inhibition at the mature adipocyte and the adipose tissue. Further, it may be confirmed that not only the adipose tissue adjacent to the skin surface, but also a visceral fat present deeply in the body such as an abdomen-deposited fat may be decomposed and may not be deposited by applying the microneedle containing the gelatin composition in accordance with the present disclosure onto the skin or deeply injecting the gelatin composition in accordance with the present disclosure into the body. In addition, it may be confirmed that the gelatin in the gelatin composition in accordance with the present disclosure may be released in a sustained manner by adjusting the cross-linking degree of the gelatin. Further, in particular, it may be confirmed that the localized obesity may be effectively treated for a long time in the region where the microneedle is applied when the microneedle containing the gelatin composition is applied.

Although the present disclosure has been described in reference with a preferred embodiment, it will be understood that various modifications, and alterations may be made to the present disclosure by those skilled in the art without departing from the spirit and scope in accordance with the present disclosure as defined in the appended claims.

What is claimed is:

1. A method for treating an individual having localized obesity, the method comprising administering a composition comprising animal-derived gelatin to the individual at a location where the individual has localized obesity,
   wherein the composition is administered by injection with a hypodermic needle or with a microneedle to skin tissue below the skin stratum corneum, and
   wherein the composition reduces adipocyte size in adipose tissue at the location where the individual has localized obesity.

2. The method of claim 1, wherein the composition is administered with the hypodermic needle.

3. The method of claim 1, wherein the individual is obese.

4. The method of claim 1, wherein the animal derived gelatin is a swine-derived gelatin.

5. The method of claim 1, wherein the animal derived gelatin is cross-linked.

6. The method of claim 5, wherein the cross-linked gelatin is cross-linked with genipin.

7. The method of claim 1, wherein the composition is administered with the microneedle.

8. The method of claim 7, wherein the microneedle comprises a tip portion having a length equal to or greater than a thickness of a skin stratum corneum of the individual.

9. The method of claim 8, wherein the microneedle is applied onto skin of the individual and at least a portion of the tip portion of the microneedle is located below the skin stratum corneum,
   wherein the tip portion comprises the composition, and
   wherein the tip portion decomposes at a position below the skin stratum corneum such that the composition is released from the tip portion and locally decomposes adipose tissue and locally inhibits lipogenesis and fat-deposition.

10. The method of claim 8, wherein the tip portion has a length of 10 µm to 300 µm.

11. The method of claim 10, wherein the microneedle further comprises a patch layer having a surface on which the tip portion is disposed.

12. The method of claim 11, wherein the patch layer is in contact with the skin and at least a portion of the tip portion is located below the skin stratum corneum.

* * * * *